United States Patent
Fish et al.

(10) Patent No.: US 10,576,000 B2
(45) Date of Patent: Mar. 3, 2020

(54) SYSTEMS AND METHODS FOR SUPPLYING POWER TO REMOVABLE STORAGE COMPARTMENTS

(71) Applicant: 19LABS INC., Menlo Park, CA (US)

(72) Inventors: Ram Adva Fish, Menlo Park, CA (US); Gerald Charles Horel, British Columbia (CA); Trevor Carter Charmley, Victoria (CA); David Miguel Moreira Goncalves, Lagos (PT)

(73) Assignee: 19Labs Inc., San Mateo, CA (US)

( * ) Notice: Subject to any disclaimer, the term of this patent is extended or adjusted under 35 U.S.C. 154(b) by 214 days.

(21) Appl. No.: 15/480,557

(22) Filed: Apr. 6, 2017

(65) Prior Publication Data

US 2017/0294781 A1 Oct. 12, 2017

Related U.S. Application Data

(60) Provisional application No. 62/320,253, filed on Apr. 8, 2016, provisional application No. 62/325,943, filed on Apr. 21, 2016.

(51) Int. Cl.
*H02J 4/00* (2006.01)
*A61F 17/00* (2006.01)
*H05K 1/02* (2006.01)
*H02J 7/00* (2006.01)

(52) U.S. Cl.
CPC .......... *A61F 17/00* (2013.01); *H02J 7/0045* (2013.01); *H05K 1/028* (2013.01)

(58) Field of Classification Search
CPC .......... H05K 1/028; H02J 7/0045; A61F 17/00
See application file for complete search history.

(56) References Cited

U.S. PATENT DOCUMENTS

| | | | |
|---|---|---|---|
| 5,355,627 A | 10/1994 | Katz | |
| 5,661,978 A | 9/1997 | Holmes et al. | |
| 6,124,707 A | 9/2000 | Kim | |
| 6,169,249 B1 * | 1/2001 | Teachout | H05K 7/1421 174/559 |
| 6,267,606 B1 * | 7/2001 | Poplawski | C07D 491/22 361/752 |
| 8,727,456 B1 | 5/2014 | Bullock et al. | |
| 2002/0171335 A1 | 11/2002 | Held | |
| 2005/0015115 A1 | 1/2005 | Sullivan et al. | |
| 2007/0173133 A1 | 7/2007 | Carlson | |
| 2007/0274042 A1 | 11/2007 | Jackson et al. | |
| 2009/0096336 A1 | 4/2009 | Petrick et al. | |

(Continued)

*Primary Examiner* — Alfonso Perez Borroto
*Assistant Examiner* — Esayas G Yeshaw
(74) *Attorney, Agent, or Firm* — Jim H. Salter; Inventive Law Inc.

(57) ABSTRACT

Provided are systems and methods for supplying electric power to removable storage compartments. The system includes an alignment body and a removable storage compartment. The alignment body is configured to align the storage compartment at a certain position, and includes a first conductive strip configured to be connected to ground, and a second conductive strip having positive voltage. The storage compartment includes at least a first and a second contact means. The first contact means is configured to be in contact with the first conductive strip, and the second contact means is configured to be in contact with the second conductive strip.

17 Claims, 3 Drawing Sheets

(56) References Cited

U.S. PATENT DOCUMENTS

| | | | |
|---|---|---|---|
| 2013/0052502 A1* | 2/2013 | Su | H02J 7/0045 |
| | | | 429/99 |
| 2013/0067248 A1 | 3/2013 | Wang | |
| 2013/0183562 A1* | 7/2013 | Workman | H01M 2/1022 |
| | | | 429/100 |
| 2014/0046482 A1* | 2/2014 | Michael | A61J 7/0084 |
| | | | 700/236 |
| 2014/0211377 A1 | 7/2014 | Graf | |
| 2016/0056430 A1* | 2/2016 | Burkman | H01M 2/1077 |
| | | | 429/99 |
| 2016/0154290 A1* | 6/2016 | Brown | H04L 12/4625 |
| | | | 359/275 |
| 2017/0245334 A1* | 8/2017 | Zhang | H02J 7/0068 |

\* cited by examiner

SYSTEMS AND METHODS FOR SUPPLYING POWER TO REMOVABLE STORAGE COMPARTMENTS

FIELD OF THE INVENTION

The present disclosure generally relates to systems and methods for supplying power to removable storage compartments, and more specifically to systems and methods for supplying power or for supplying power and enabling data transmission to removable storage compartments in medical appliances.

BACKGROUND

Some systems, e.g., medical systems, may include several independent devices that together form an entire system. Many devices, specifically medical devices, require electrical power in order to operate. Therefore, some medical systems require the presence of wires and a power supply in close proximity to the location of the medical system. Supplying power to devices via wires, specifically to medical devices, is very limiting. This is due to the fact that medical devices are typically required to be moved from one location to another, e.g., when moved from one patient to another, whereby some locations may not be equipped with power supply, or it may be time consuming to connect the devices' wires to a power supply when a clinician needs to operate such devices without any interruption.

Nowadays, some devices are operated by batteries, or rechargeable batteries, but such devices require continuous monitoring of the status of the batteries in order to ensure the devices are ready for operation at all times.

SUMMARY

According to an aspect of some embodiments of the present invention there is provided a system for supplying electric power to a removable storage compartment that is configured to store electrical devices therein, and thus to supply power to the stored devices. The system may include an alignment body configured to align a storage compartment at a certain position, a first conductive strip configured to be connected to ground, a second conductive strip having positive voltage, and at least a first and a second contact means, whereby the first contact means may be configured to be in contact with the first conductive strip, and the second contact means may be configured to be in contact with the second conductive strip. In some embodiments, the first and second conductive strips may be positioned along the alignment body, and the at least first and second contact means may be positioned along the storage compartment.

In some embodiments, the alignment body may comprise a proximal end that is located in close proximity to a user handling the storage compartment and the alignment body, and a distal end that is located farther away from the user.

According to some embodiments, the first and second contact means may be pogo pins.

In some embodiments, the first and second conductive strips may be connected to a PCB. In some embodiments, the PCB may be a flexible PCB.

According to some embodiments, the storage compartment may be a drawer. In some embodiments, the storage compartment may be part of a medical appliance. The medical appliance may be an interactive first aid kit.

In some embodiments, the storage compartment may be configured to supply power to at least one electrical device that is stored within the storage compartment.

According to some embodiments, the storage compartment may comprise power holes configured to provide power to the at least one electrical device, when the device is connected to the power holes via wires. In some embodiments, the storage compartment may comprise at least one USB connector configured to power a USB cable, whereby the USB cable is connected on one end to the at least one USB connector, and on the opposite end to the at least one electrical device.

In some embodiments, the system may further comprise data lines positioned along the alignment body. The data lines may be configured to enable data transmission from the storage compartment to an external device and from an external device to the storage compartment.

In some embodiments, the first conductive strip may be longer than the second conductive strip. In some embodiments, the first conductive strip may be located closer to the proximal end of the alignment body than the location of the second conductive strip.

In some embodiments, the first contact means may be configured to contact the first conductive strip before the second contact means contacts the second conductive strip.

According to another aspect of some embodiments of the present invention there is provided a method for supplying electric power to a removable storage compartment, such to supply power to electrical devices stored within the storage compartment. The method may include: providing a storage compartment comprising at least a first and second contact means, providing at least two alignment bodies, wherein one of the at least two alignment bodies comprising a first conductive strip configured to be connected to ground, and a second conductive strip having positive voltage, inserting the storage compartment between the at least two alignment bodies such that the first contact means is in contact with the first conductive strip, and the second contact means is in contact with the second conductive strip, and supplying power to the storage compartment.

In some embodiments, the first contact means may be configured to contact the first conductive strip before the second contact means contacts the second conductive strip.

In some embodiments, the method may comprise pushing and pulling the storage compartment back and forth between the at least two alignment bodies.

According to some embodiments, the method may further comprise supplying power to at least one electrical device stored within the storage compartment. In some embodiments, supplying power to the at least one electrical device may be performed by connecting the at least one electrical device via wires to power holes comprised within the storage compartment. In other embodiments, supplying power to the at least one electrical device may be performed by connecting the at least one electrical device via wires to a USB connector comprised within the storage compartment.

In some embodiments, the method may further comprise enabling data transmission from the storage compartment to an external device, and from an external device to the storage compartment, via data lines positioned on one of the at least two alignment bodies.

BRIEF DESCRIPTION OF THE DRAWINGS

Some non-limiting exemplary embodiments or features of the disclosed subject matter are illustrated in the following drawings.

Figure 1:
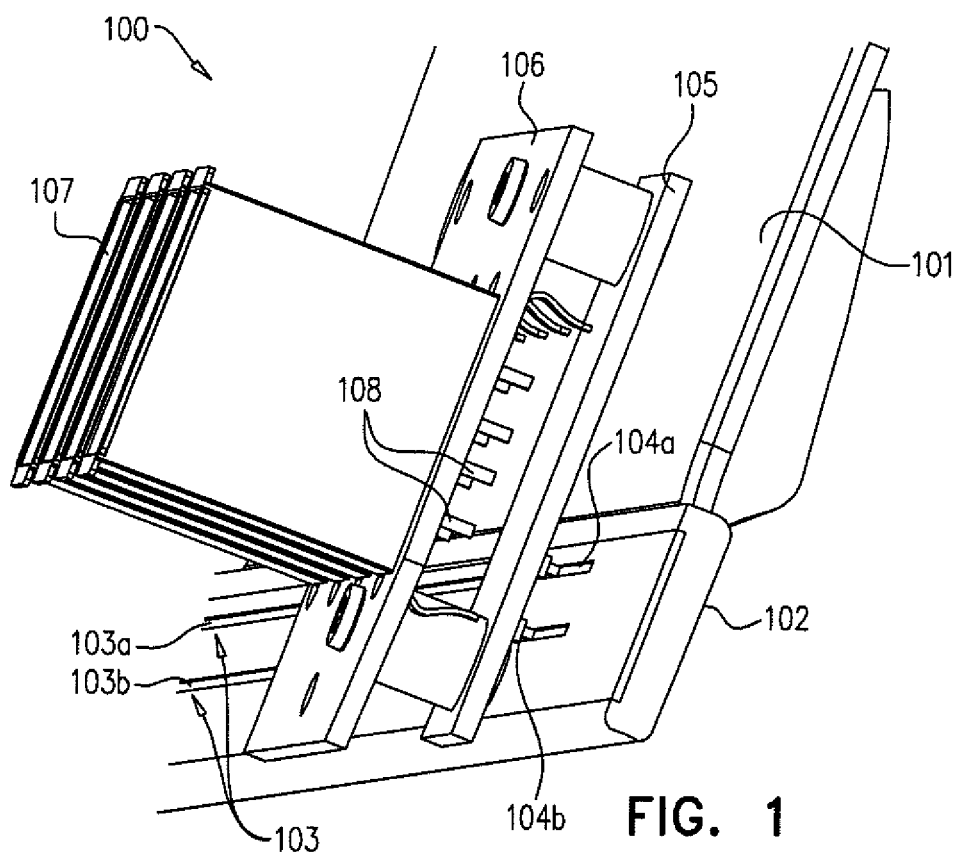
FIG. 1 is a schematic illustration of a respective view of a system for supplying power to a removable storage compartment, according to some embodiments of the present invention.

With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

Some embodiments of the present invention provide systems for supplying power to removable storage compartments, e.g., drawers, which may be part of electrical appliances, e.g., electrical medial appliances. As mentioned above, some known systems that require power for their operation, may be powered either via wires or via batteries. However, as mentioned above, such systems are very limited with respect to their operation, as well as with respect to their mobility. Systems that are powered via wires are limited with respect to operation, since their operation is restricted by the need to connect the system to a power source via wires. This also affects mobility of such systems, since mobility is limited to locations where a power source suitable for supplying power via wires, e.g., an electrical outlet or wall socket, is available. Systems that include batteries, whether rechargeable or non-rechargeable, are also limited in the sense that the status of batteries should be constantly monitored in order to ensure the systems are supplied with enough power for proper operation.

The system provided according to some embodiments of the present invention, enables supplying power to devices stored within removable storage compartments by supplying power to the removable storage compartments, e.g., removable drawers. Such removable drawers may be part of a system, e.g., an interactive first aid kit system that is configured to store various medical devices, which operation depends on electrical power. For example, a first aid kit system may include a thermometer, a pulse oximeter, a blood pressure measuring device, a stethoscope, an otoscope, etc. These devices may require power in order to properly operate. Thus, connecting these and similar or other devices to a drawer that receives power supply, and thus provides continuous power to these devices, when the drawer is closed or even when the drawer is partially open, ensures such devices are constantly powered and ready for operation at any location.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a respective view of a system for supplying power to a removable drawer, according to some embodiments of the present invention. System 100 may comprise an alignment body 101 that is configured to align the position and location of a storage compartment (110, FIG. 2) at a certain position, such that power is properly supplied to the storage compartment. Typically, two alignment bodies 101 may be located on the opposing sides of a storage compartment, such to support the opposing sides of a storage compartment that is inserted between the two alignment bodies 101 (see FIG. 3). In some embodiments, each of the two alignment bodies 101 may be divided into two parts, one supporting the top end and one supporting the bottom end of the two opposing sides of a storage compartment that is inserted between the two alignment bodies 101 (described in detail with respect to alignment bodies 101a and 101b, FIG. 3).

In some embodiments, the storage compartment may be a removable drawer.

In some embodiments, alignment body 101 may have attached a printed circuit board (PCB) 102, which may be a flexible PCB or a rigid PCB. In some embodiments, PCB 102 may have attached conductive strips 103. Conductive strips 103 may comprise at least two conductive strips 103a and 103b, whereby first conductive strip 103a may be configured to be attached to ground (GND), while second conductive strip 103b may provide positive voltage, for example, +5V. However, in other embodiments, any other amount of voltage may be carried by second conductive strip 103b.

According to some embodiments, PCB 102 may have attached thereon more than two conductive strips (e.g., strips 103a and 103b). In such embodiments, PCB 102 may have attached additional conductive strips (not shown) configured to enable data transmission. For example, one conductive strip may be +D, and another conductive strip may be −D. Data transmission may be important when data from the devices carried by the storage compartment is to be sent to an external device, e.g., a computerized device, or when data is to be received by the devices stored within the storage compartment from an external device. For example, if the storage compartment contains medical devices, e.g., an oximeter, and a thermometer, the last few measurements acquired by the oximeter and the thermometer should typically be transmitted to a physician's external device, e.g., a laptop, in order to enable the physician to monitor status of the patient for which such measurements were acquired. In other embodiments, the physician may wish to send a command to operate the oximeter and thermometer in order to obtain measurements of a patient. For example, post-surgical operation, a patient's vital signs should be monitored in order to determine whether the patient's recovery is as expected. In such case, the physician may use his remote device, e.g., laptop, to send a command to a medical device contained within the storage compartment, e.g., an oximeter and thermometer. These devices may then execute some kind of alert (e.g., the devices may make an alert sound), such that a healthcare provider that is in close proximity to the storage compartment, may notice the alert and operate the devices to acquire the requested measurements from the patient. That is, communication and data transmission may be enabled in a bi-directional manner, via data lines that may be positioned on PCB 102, and thus on alignment body 101.

In other embodiments, other types and/or numbers of conductive strips may be implemented as part of system 100.

In order to provide power supply to a storage compartment (e.g., storage compartment 110, FIG. 2), contact is required between the conductive strips, e.g., conductive strips 103a and 103b, and the storage compartment. Thus, the storage compartment may comprise contact means 104 that may be configured to be in contact with the conductive strips. In some embodiments, a first contact means 104a may be configured to contact first conductive strip 103a, and second contact means 104b may be configured to contact second conductive means 103b. If a larger number of conductive strips is attached onto PCB 102, then a corresponding number of contact means 104 may be used.

In some embodiments, contact means 104 may be pogo pins, though any other type of contact means may be used.

According to embodiments of the present invention, the alignment body(ies) 101 may dictate the distance between the conductive strips 103 and the contact means 104, such to enable proper contact between contact means 104 and conductive strips 103.

In some embodiments, contact means 104 may be connected to a PCB 105. In some embodiments, the contact means 104, e.g., pogo pins may be soldered into PCB 105.

In some embodiments, in order to provide power to devices contained within the storage compartment, the storage compartment may comprise connectors 107, e.g., USB type connectors. Connectors 107 may be configured to accept corresponding plugs, which may be attached to various devices contained within the storage compartment. For example, USB connectors 107 may be configured to accept USB plugs that are connected to electrical devices, such to provide electrical power to these devices via USB connectors 107. That is, a USB plug may connect between an electrical device and USB connector 107.

In some embodiments, connectors 107 may be connected to a PCB 106. In some embodiments, connectors 107 may be soldered in PCB 106.

According to some embodiments, the distance between PCB 105 and conductive strips 103 may be predetermined and may be dictated by the operation-compression of contact means 104, e.g., of pogo pins 104a and 104b. That is, pogo pins 104 require a specific compression applied onto them in order to properly operate, for example, the distance between PCB 105 and conductive strips 103 may be between 4.25 mm-4.45 mm, in order to apply suitable pressure onto pogo pins 104 enabling the pogo pins 104 to provide the required electrical connection between PCB 105 and conductive strips 103.

In some embodiments, the location of PCB 106 may be dictated by the internal arrangement of electrical devices that are to be contained by the storage compartment. For example, USB connector 107 needs to be aligned with respect to the internal space of the storage compartment.

According to some embodiments, since a PCB is required to contact an external power supply in order to provide power to the storage compartment, while the PCB is further required to transfer power to electrical devices contained within the storage compartment, and since there are different constraints with respect to the distance between the PCB and the external and the internal connections, system 100 may comprises two PCBs. PCB 105 is to be in contact with conductive strips 103, which are located externally to the storage compartment, while PCB 106 is to be in contact with electrical devices contained within the storage compartment, which are located internally to the storage compartment.

According to some embodiments, between PCB 105 and PCB 106 there may be distance means 108 configured to control the distance between PCB 105 and PCB 106, as well as being made of a conductive material, such to properly provide power to connectors 107 via contact means 104, which are in contact with conductive strips 103. In some embodiments, distance means 108 may be pins of a certain length, which may be located between PCB 105 and PCB 106. In some embodiments, distance means 108 may be flexible pins such to enable adjustment of the distance between PCB 105 and PCB 106, while in other embodiments distance means 108 may be rigid pins of a predetermined length dictated by the constraints discussed hereinabove in detail. In other embodiments, distance means 108 may be a cable(s) connecting between PCB 105 and PCB 106.

According to some embodiments, the storage compartment may be power supplied when inserted all the way through the two alignment bodies 101, which support the storage compartment on both of its sides, and also when the storage compartment is only partially inserted between the two alignment bodies 101. For example, if the removable storage compartment is a removable drawer, power may be supplied to the drawer when the drawer is fully inserted between and along the two alignment bodies 101, e.g., when the drawer is closed. In addition, power may be supplied to the removable drawer even when it is partially open, since the conductive strips 103 pass along substantially the entire length of the of alignment bodies 101 (e.g., along the longitudinal axis of alignment bodies 101). Thus, contact between contact means 104 and conductive strips may be enabled along substantially the entire length of conductive strips 103.

According to other embodiments, conductive strips or conductive tracks may be positioned on the storage compartment, e.g., storage compartment 110 (FIG. 2), while contact means, e.g., conductive pins or pogo pins, may be positioned on the alignment bodies 101. That is, as long as either of the components that are to be in contact with one another (e.g., a storage compartment and an alignment body) has either conductive strips/tracks or contact means (e.g., pogo pins) thereon, electric contact is enabled and thus power may be supplied via the alignment bodies to the storage compartment.

Figure 2:
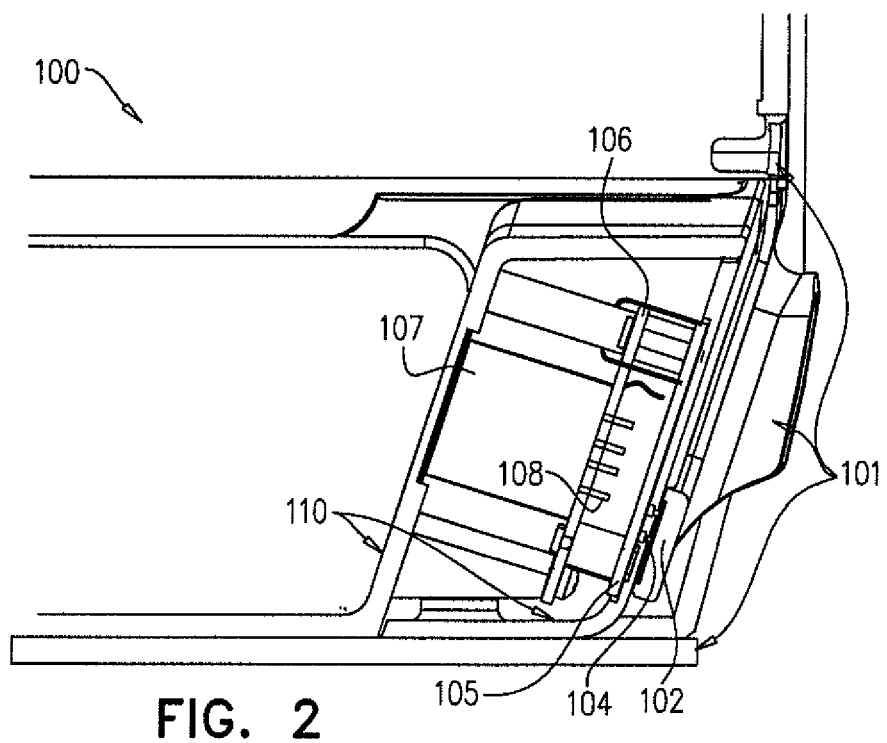
FIG. 2 is a schematic illustration of a side view of a system for supplying power to a removable storage compartment, according to some embodiments of the present invention.

Reference is now made to FIG. 2, which is a schematic illustration of a side view of a system 100 for supplying power to a removable storage compartment, according to some embodiments of the present invention. FIG. 2 illustrates storage compartment 110 as it is fully inserted along alignment bodies 101, towards the distal end of alignment body 101 (which is the end farther away from a user using system 100). Alignment bodies 101 may be located on both sides of storage compartment 110. In some embodiments, alignment bodies 101 may also be located beneath storage compartment 110, such to provide support below storage compartment 110 in addition to providing support on the typically opposing sides of storage compartment 110.

As described with respect to FIG. 1, system 100 may comprise PCB 102 that has attached conductive strips 103 (not shown). Contact means 104 may be in contact with PCB 102 via the conductive strips. Connectors 107, which may be USB type connectors, may be connected, e.g., soldered in PCB 106, while contact means 104 may be connected, e.g., soldered in PCB 105. In between PCB 105 and PCB 106 there may be distance means 108 that are configured to control the exact distance between these PCBs.

Figure 3:
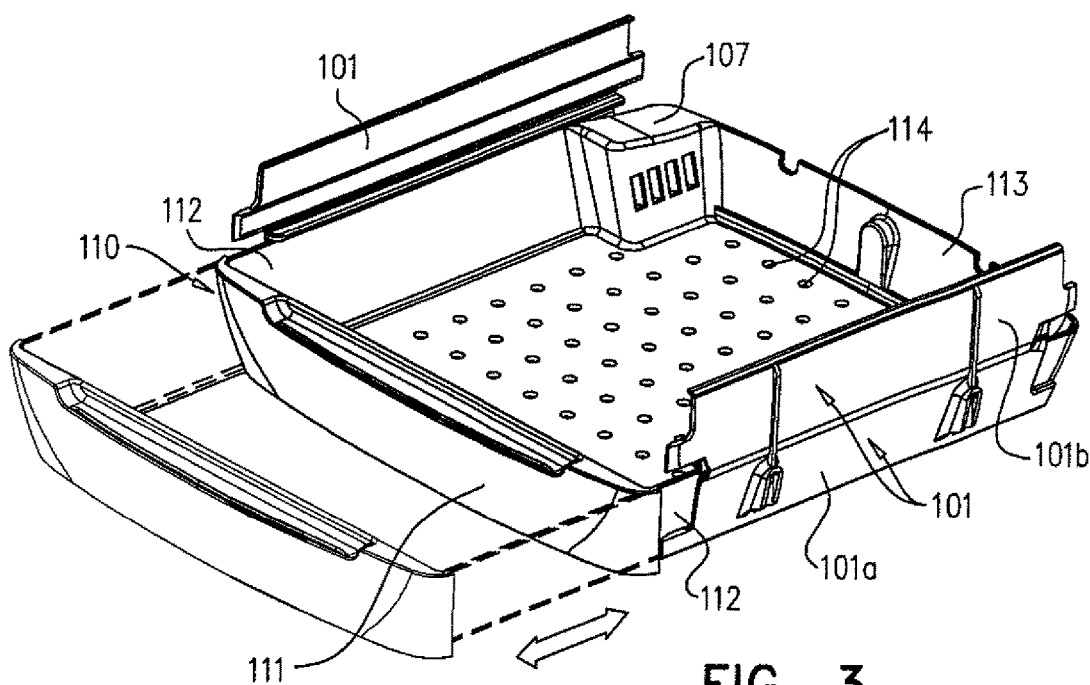
FIG. 3 is a schematic illustration of a top-side view of a system for supplying power to a removable storage compartment, according to some embodiments of the present invention.

Reference is now made to FIG. 3, which is a schematic illustration of a top-side view of a system for supplying power to a removable storage compartment, according to some embodiments of the present invention. According to some embodiments, storage compartment 110 may be comprise a front side 111, a left and right sides 112, and a back side 113. Back side 113 of storage compartment 110 may be typically inserted all the way through alignment bodies 101, towards the distal end of each of alignment bodies 101, such that front side 111 is the side visible to a user using storage compartment 110. Left and right sides 112 of storage compartment 110 may be supported by alignment bodies 101 that may be located adjacent to those exact sides. Alignment bodies 101 may comprise or be divided to a bottom end 101a and a top end 101b, such to better align the position of storage compartment 110 between two typically opposing alignment bodies 101.

According to some embodiments, connectors 107 may be located on either of the sides 112 of storage compartment 110, such to be able to contact with conductive strips 103 (FIG. 1) via contact means 104 (FIG. 1). The conductive strips 103 may be located on any one of the alignment bodies 101 that corresponds (and is adjacent to) to the side of storage compartment 110, at which connectors 107 are located. That is, if connectors 107 are located on the left side of storage compartment 110, the conductive strips may be located on the alignment body 101 that is located at the left of system 100. If connectors 107 are located on the right side of storage compartment 110, the conductive strips may be located on the alignment body 101 that is located at the right of system 100. Similarly, the location of the conductive strips may dictate the corresponding location of conneecters 107.

In some embodiments, storage compartment 110 may comprise alignment indents 114, which may be configured to accept suitable clips and/or dividers in order to arrange the space within storage compartment 110 for optimal storage. Dividers and/or clips may be inserted into alignment indents 114 such to optimally divide the space in storage compartment 110 for disposal of the various devices that are to be stored and contained within storage compartment 110.

In other embodiments, indents 114 may be 'power holes' configured to provide electrical power to devices contained within storage compartment 110. That is, electrical devices stored within storage compartment 110 may comprise connectors of any kind, which may be inserted into power holes 114 in order to receive electrical power from storage compartment 110 via power holes 114. Power holes 114 may be in electrical connection with either PCB 105 or PCB 106, such to receive electrical power from either two PCBs. That is, wires may be connected on one end to power holes 114 and on the other end to an electrical device stored with storage compartment 101.

According to some embodiments, some of indents 114 may be alignment indents that may provide the ability to align the position of devices within storage compartment 110, whereas some of indents 114 may be power holes that may provide power to the devices contained within storage compartment 110.

In some embodiments, storage compartment 110 may supply power to devices stored within via connectors 107, via power holes 114, or using both power connection means.

Figure 4A:
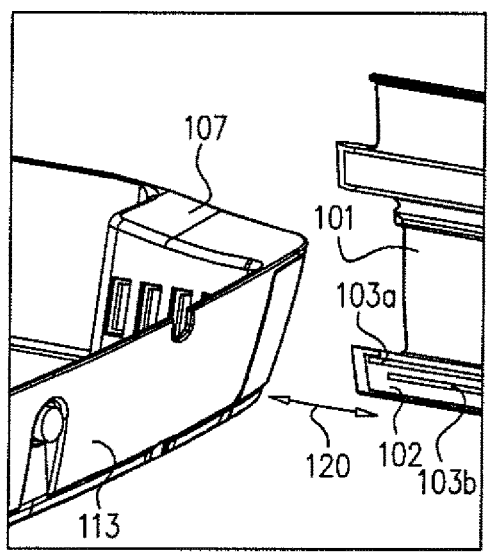
FIGS. 4A-4B are schematic illustrations of a back-side view and a side view, respectively, of a system for supplying power to a removable storage compartment prior to insertion of the storage compartment in between the alignment bodies, according to some embodiments of the present invention.
Figure 4B:
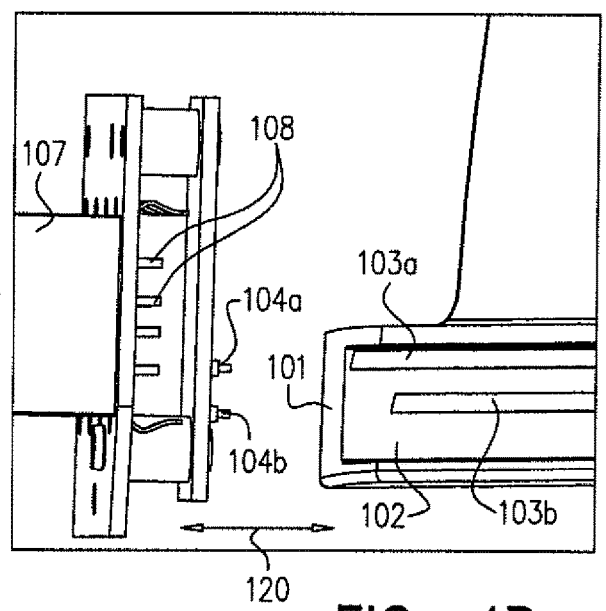

Reference is now made to FIGS. 4A-4B, which are schematic illustrations of a back-side view and a side view, respectively, of a system for supplying power to a removable storage compartment prior to insertion of the storage compartment in between the alignment bodies, according to some embodiments of the present invention.

According to some embodiments, alignment body 101 may comprise a proximal end and a distal end. The proximal end is the end of alignment body 101 that is located in close proximity and adjacent a user handling alignment body 101 and storage compartment 110, while the distal end is the end of alignment body 101 that is located farther away from the user.

As illustrated in FIG. 4A, back side 113 of storage compartment 110 is shown to be placed or slid into alignment body 101. The direction of movement of storage compartment 110 along alignment body 101 is illustrated by arrow 120. Arrow 120 illustrates a back-and-forth direction of movement, which corresponds to a closed-open state of the storage compartment 110. Storage compartment 110 may be pushed all the way through alignment bodies 101 towards the distal end of alignment body 101, until storage compartment 110 reaches its closed state. Additionally, storage compartment 110 may be pulled outside of alignment bodies 101, towards the proximal end of alignment body 101, until storage compartment 110 reaches its open state. All intermediate locations of storage compartment 110 with respect to alignment bodies 101 are intermediate states of storage compartment 110 between its open state and its closed state.

As illustrated in FIG. 4B, when storage compartment 110 moves in the backwards direction illustrated by arrow 120, that is, when storage compartment 110 moves adjacent to alignment body 101 and along the longitudinal axis of alignment body 101 towards the distal end of alignment body 101, contact means 104 may contact conductive strips 103. For example, once storage compartment 110 is slid along the longitudinal axis of alignment body 101 towards its distal end, contact means 104a may contact conductive strip 103a, and contact means 104b may contact conductive strip 103b.

In some embodiments, conductive strip 103a may be longer than conductive strip 103b, and may begin at a location that is closer to the proximal end of alignment body 101 compared to the location where conductive strip 103b begins. This is in order to ensure that contact means 104a first contacts ground, and only then would contact means 104b contact the conductive strip that possess positive voltage, thus avoiding the possibility of electrocution of a user handling the storage compartment 110.

According to some embodiments, the location and/or position of the conductive strips (or tracks) and of the contact means on either of the storage compartment or alignment bodies may be at any corresponding location along the storage compartment and the alignment bodies. For example, as illustrated in FIGS. 1-3, the location of the conductive strips on the alignment bodies is adjacent to the sides of the storage compartment 110, and thus the contact means 104 are located on the sides of storage compartment 110. However, in other embodiments, the contact means may be located at the bottom of the storage compartment, while the conductive strips may be located at the bottom end of the alignment bodies. In yet other embodiments, the conductive strips may be located at the bottom of the storage compartment, while the contact means may be located at the bottom end of the alignment bodies. Thus, when the storage compartment is inserted in between two alignment bodies that comprise a mutual bottom alignment body, the conductive strips on the storage compartment come in contact with the contact means that are located on the bottom alignment body, since the bottom side of the storage compartment becomes adjacent to the bottom alignment body when inserted through the two sided alignment bodies. Electric contact may then take place between the storage compartment's conductive strips or tracks and the alignment body's contact means such to supply power to the storage compartment via the alignment body, which may be supplied with power via an external power source.

Figure 5:
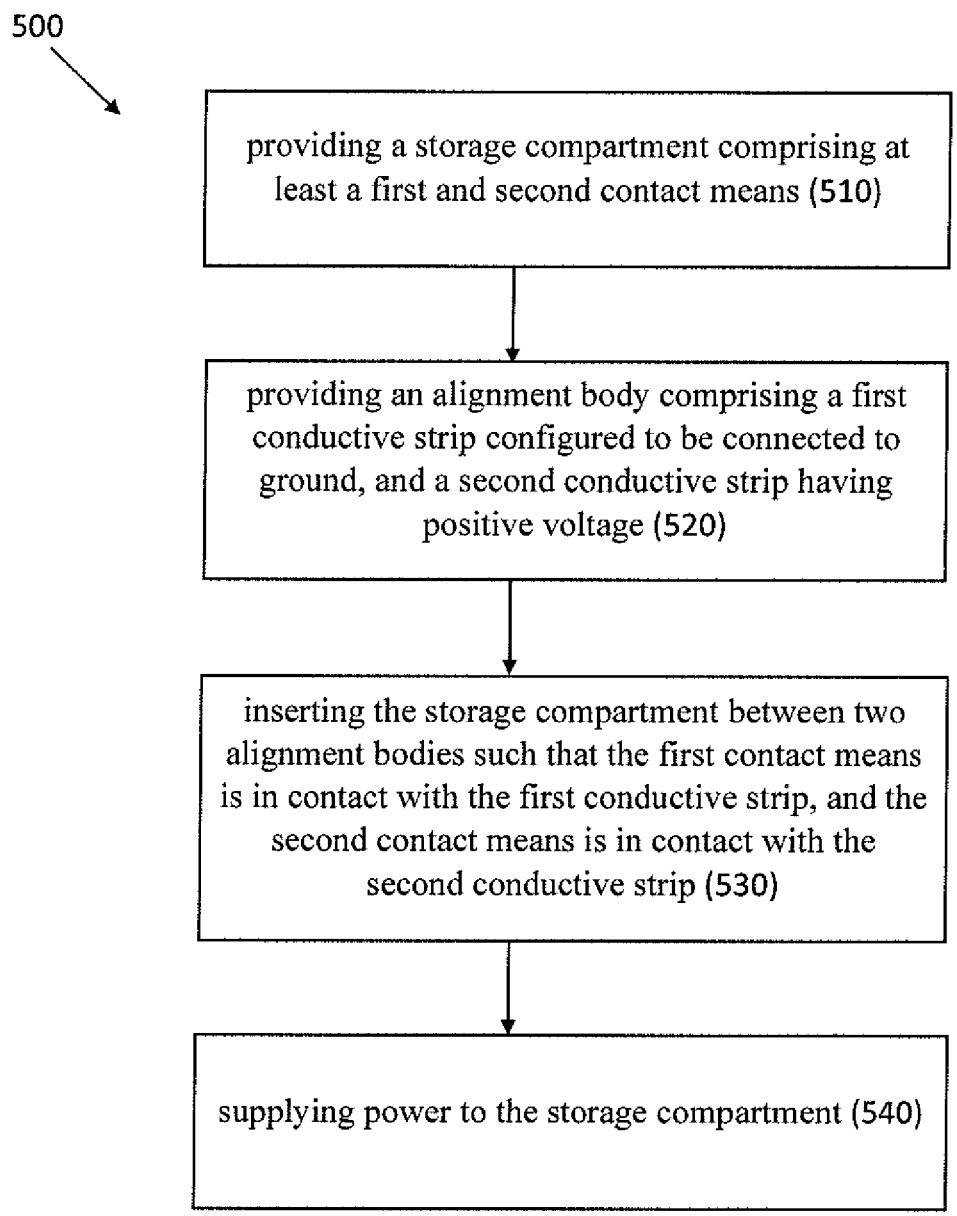
FIG. 5 is a flow chart illustrating a method for supplying power to a removable storage compartment, according to some embodiments of the present invention.

Reference is now made to FIG. 5, which is a flow chart illustrating a method for supplying power to a removable storage compartment, according to some embodiments of the present invention. Method 500 may comprise providing a storage compartment comprising at least a first and second contact means, as disclosed in box 510. Method 500 may further comprise providing a t least one alignment body comprising a first conductive strip configured to be connected to ground, and a second conductive strip having positive voltage, as disclosed in box 520. In some embodiments, the method may further comprise inserting the storage compartment between two alignment bodies such that the first contact means is in contact with the first conductive strip, and the second contact means is in contact with the second conductive strip, as disclosed in box 530. In some embodiments, at least one of the two alignment bodies comprises the first and second conductive strips. According to some embodiments, as a result of the first contact means being in contact with the first conductive strip, and the second contact means being in contact with the second conductive strip, the method comprises supplying power to the storage compartment, as disclosed in box 540.

According to some embodiments, the first contact means is configured to contact the first conductive strip before the second contact means contacts the second conductive strip.

According to some embodiments, a method for supplying power to removable storage compartment, e.g., method 500 may further comprise pushing and pulling the storage compartment back and forth between the at least two alignment bodies, e.g., between the distal and proximal ends of the two alignment bodies.

In some embodiments, the method may further comprise supplying power to at least one electrical device stored within the storage compartment. The electrical devices stored within the storage compartment may be medical type devices, e.g., oximeter, thermometer, otoscope, stethoscope, etc.

In some embodiments, supplying power to the at least one electrical device is performed by connecting the at least one electrical device via wires to power holes comprised within the storage compartment. In some embodiments, supplying power to the at least one electrical device is performed by connecting the at least one electrical device via wires to a USB connector comprised within the storage compartment. In other embodiments, supplying power to the at least one electrical device is performed by connecting the at least one electrical device via wires to power holes, and by connecting the at least one electrical device via wires to a USB connector.

In some embodiments, method 500 may further comprise enabling data transmission from the storage compartment to an external device, and from an external device to the storage compartment, via data lines positioned on one of the at least two alignment bodies. Data transmission may comprise sending acquired measurements from the electrical devices stored in the storage compartment to an external device, e.g., a physician's computerized device, or sending commands from an external device to the electrical devices stored in the storage compartment.

In the context of some embodiments of the present disclosure, by way of example and without limiting, terms such as 'operating' or 'executing' imply also capabilities, such as 'operable' or 'executable', respectively.

Conjugated terms such as, by way of example, 'a thing property' implies a property of the thing, unless otherwise clearly evident from the context thereof.

In case electrical or electronic equipment is disclosed it is assumed that an so appropriate power supply is used for the operation thereof.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. A system for supplying electric power to a storage compartment, said system comprising:
   an alignment body configured to align a storage compartment at a certain position, said alignment body comprising a proximal end and a distal end;
   a first conductive strip configured to be connected to ground;
   a second conductive strip having positive voltage;
   at least a first and second contact means, wherein the first contact means is configured to be in contact with the first conductive strip, and wherein the second contact means is configured to be in contact with the second conductive strip; and
   wherein said first and second conductive strips are positioned along said alignment body, wherein said at least first and second contact means are pogo pins positioned along the storage compartment, and
wherein the storage compartment is part of a medical appliance.

2. The system according to claim 1, wherein the first and second conductive strips are connected to a PCB.

3. The system according to claim 2, wherein the PCB is a flexible PCB.

4. The system according to claim 1, wherein the storage compartment is a drawer.

5. The system according to claim 1, wherein the medical appliance is an interactive first aid kit.

6. The system according to claim 1, wherein the storage compartment is configured to supply power to at least one electrical device that is stored within the storage compartment.

7. The system according to claim 6, wherein the storage compartment comprises power holes configured to provide power to the at least one electrical device, when the device is connected to the power holes via wires.

8. The system according to claim 6, wherein the storage compartment comprises at least one USB connector configured to power a USB cable, wherein said USB cable is connected on one end to the at least one USB connector, and on the opposite end to said at least one electrical device.

9. The system according to claim 1, wherein the system further comprises data lines positioned along the alignment body, said data lines configured to enable data transmission from the storage compartment to an external device and from an external device to the storage compartment.

10. The system according to claim 1, wherein the first conductive strip is longer than the second conductive strip and further wherein the first conductive strip is located closer to the proximal end of the alignment body than the location of the second conductive strip.

11. The system according to claim 1, wherein the first contact means is configured to contact the first conductive strip before the second contact means contacts the second conductive strip.

12. A method for supplying electric power to a storage compartment, said method comprising:
providing a storage compartment comprising at least a first and second contact means, said at least first and second contact means are pogo pins positioned along the storage compartment;
providing at least two alignment bodies, wherein one of the at least two alignment bodies comprising a first conductive strip configured to be connected to ground, and a second conductive strip having positive voltage;
inserting the storage compartment between the at least two alignment bodies such that the first contact means is in contact with the first conductive strip, and the second contact means is in contact with the second conductive strip; and
supplying power to the storage compartment,
wherein the first contact means is configured to contact the first conductive strip before the second contact means contacts the second conductive strip.

13. The method according to claim 12, further comprising pushing and pulling the storage compartment back and forth between the at least two alignment bodies.

14. The method according to claim 12, further comprising supplying power to at least one electrical device stored within the storage compartment.

15. The method according to claim 14, wherein supplying power to the at least one electrical device is performed by connecting the at least one electrical device via wires to power holes comprised within the storage compartment.

16. The method according to claim 14, wherein supplying power to the at least one electrical device is performed by connecting the at least one electrical device via wires to a USB connector comprised within the storage compartment.

17. The method according to claim 12, further comprising enabling data transmission from the storage compartment to an external device, and from an external device to the storage compartment, via data lines positioned on one of the at least two alignment bodies.

* * * * *